United States Patent [19]

Calhoun

[11] Patent Number: 5,156,813
[45] Date of Patent: Oct. 20, 1992

[54] CUP FOR USE WITH A PIPETTE PROBE

[75] Inventor: Jeffrey Calhoun, Peekskill, N.Y.

[73] Assignee: Medical Laboratory Automation, Inc., Pleasantville, N.Y.

[21] Appl. No.: 552,434

[22] Filed: Jul. 13, 1990

[51] Int. Cl.$^5$ .................................. B01L 3/00
[52] U.S. Cl. ......................... 422/102; 422/104; 215/307; 215/309; 215/364; 134/135; 134/150; 134/155; 134/166 R; 134/166 C; 134/170; 134/186; 73/864.22
[58] Field of Search .............. 422/104, 102; 222/148; 215/309, 307, 248, 364; 73/864.22; 134/135, 150, 155, 166 C, 166 R, 170, 186

[56] References Cited

U.S. PATENT DOCUMENTS

| | | | |
|---|---|---|---|
| 3,813,223 | 5/1974 | Fleck | 422/102 |
| 4,121,525 | 11/1978 | Courtis | 215/248 |
| 4,730,631 | 3/1988 | Schwart | 134/155 |
| 4,888,998 | 12/1989 | Buzz et al. | 75/864.22 |
| 4,989,623 | 2/1991 | Hoffman et al. | 134/170 |

Primary Examiner—James C. Housel
Assistant Examiner—Maureen M. Wallenhorst
Attorney, Agent, or Firm—Wolf, Greenfield & Sacks

[57] ABSTRACT

A fluid cup is provided for use with a cup support having a cup-receiving receptacle and a drain. The cup is adapted for use with a pipette probe which may introduce contaminants into the fluid, for example a dilutant fluid, in the cup. The cup has a lower cup portion and a cap, with a notch or other overflow element being provided near the top of the lower cup portion. Diluent fluid is introduced near the bottom of the lower cup portion after each probe entry, creating a fluid flow pattern which flushes any contaminant from the cup through the notch without requiring the use of a large fluid volume.

5 Claims, 1 Drawing Sheet

CUP FOR USE WITH A PIPETTE PROBE

FIELD OF THE INVENTION

This invention relates to equipment for mixing precise quantities of fluids and, more particularly, to a cup for use in such systems which permits contaminants from a prior use of the cup to be easily removed while assuring that a precisely controlled quantity of fluid is in the cup at any given time.

BACKGROUND OF THE INVENTION

Electronic pipette systems are utilized to mix precise quantities of various fluids. For example, it may be desired to dilute blood samples or samples of other bodily fluids with a diluent such as saline water before further processing the samples. In order to assure that the results of tests conducted from such diluted samples are accurate, the quantities of both the bodily fluid sample and the diluent must be carefully controlled. These goals may be accomplished in current pipette systems by initially drawing a precise quantity of diluant into the probe. Next a separator air bubble is aspirated, followed by a precise quantity of the fluid sample. The diluent and sample mix when they are dispensed one after the other into an analytical cuvette. Before the next diluent or sample is aspirated into the pipette probe, the probe is washed with a rinse solution. This removes most of the contamination left on the inside and/or outside surfaces of the probe tip from the previous sample.

In order to assure an adequate diluent supply the diluent cup is designed to fill to a precise level. The electronics of the system can detect this level, and thereby confirm that there is adequate diluent supply in the system. If the electronics do not detect liquid at this level, the user is alerted to replenish the diluent supply bottle. Diluent in the cup may all be removed except for the dead volume of the cup which may, for example, be the last 100 micro liters.

One problem with systems of the type described above is that, even with a wash between the taking of a bodily fluid sample and a diluent sample, it is still possible for some of the bodily fluid to adhere to the pipette and to be left behind as a residue in the diluent. This residue may contaminate future samples to be diluted from the same cup and is, therefore, undesirable. However, it is desirable that large quantities of diluent not be required to flush such contaminating residue from the cup between samples.

Apparatus should, therefore, be provided to assure that such contaminants are flushed from the cup containing the diluent or other fluid to be mixed with a bodily fluid sample before a subsequent use so as to avoid contamination. Such apparatus should probably require the use of a minimum quantity of diluent fluid to perform the flush operation.

SUMMARY OF THE INVENTION

It is, therefore, a primary object of this invention to provide an improved cup assembly for use with a pipette or other fluid drawing probe to assure that any contaminants on the probe are efficiently flushed from the system between uses.

In accordance with the above, this invention provides a cup element, such as a diluent cup, for use with a cup support having a cup receiving receptacle and a drain. The cup has a lower cup portion sized to fit in the cup receiving receptacle. An overflow notch is formed in the upper part of the cup portion, for example in at least one side thereof, the notch extending from the top lip of the cup portion to a predetermined depth, the notch permitting fluid in the cup portion above such depth to overflow to the drain. A straw or other suitable means is provided for introducing the fluid at a point below the notch, preferably to the bottom of the cup portion. This creates a flow pattern which flushes any contaminant residue from the cup through the notch. For the preferred embodiment, the straw is fixed in an upright position in a cap which snap-fits in the lip of the cup portion and an opening is provided in the cap through which a pipette probe may be inserted. The probe is preferably adjacent the notch when in the opening. Means are provided for assuring that the cup portion is oriented in the recess in a manner such that the notch is adjacent the drain.

The foregoing and other objects, features and advantages of the invention will be apparent from the following more particular description of a preferred embodiment of the invention as illustrated in the accompanying drawings.

IN THE DRAWINGS

DETAILED DESCRIPTION

Figure 1:
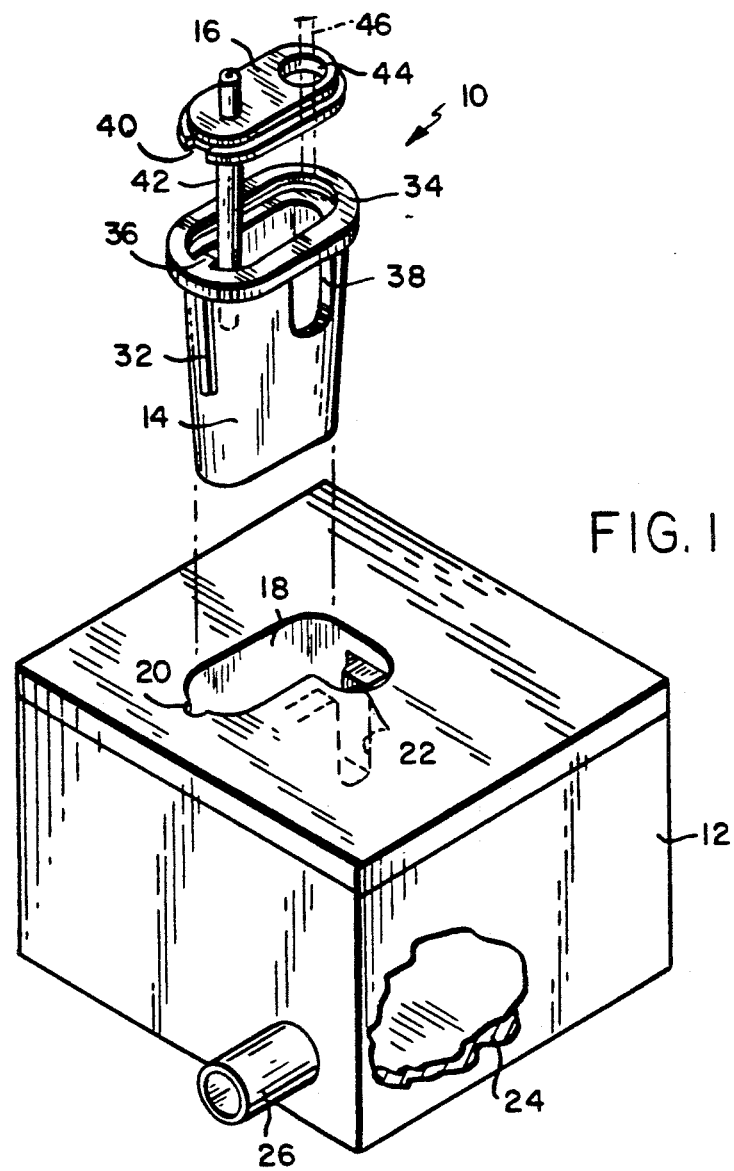
FIG. 1 is a partially exploded, partially cut-away perspective view of a diluent cup and cup support assembly in accordance with a preferred embodiment of the invention.

Referring to the figures, the diluent cup assembly 10 includes a cup base support 12, a lower cup portion 14, and a cup cap 16. Base support 12 has a cup receiving recess 18 formed therein. At one end of recess 18 is an orientation notch 20. A channel 22 is provided on one side of recess 18, which channel ends inside support 12 in a chamber 24. A drain pipe 26 extends from the bottom of chamber 24. Drain pipe 26 may be connected to a suitable drain hose, tubing or other suitable means for the removal of waste fluid. Support 12 is formed of a hard nonconductive material, preferably a plastic such as ABS.

Lower cup portion 14 has tapered side and ends walls and a generally oval cross section. The bottom of cup portion 14 has a small well 30 formed therein. An orientation projection 32 extends from one end and coacts with orientation notch 20 to assure that the cup portion 14 can be inserted in recess 18 in only one orientation. The upper end of cup portion 14 is formed into an overhanging flexible lip 34. A projection 36 is formed in one end of lip 34, for example, the end adjacent projection 32. A round indentation or notch 38 is formed in the side of cup portion 14 which is adjacent channel 22 when cup portion 14 is properly oriented in recess 18. Notch 38 extends from lip 34 to a depth such that the level and volume of fluid 41 in the cup portion when the cup portion is filled to the bottom of notch 38 as shown in FIG. 2 is equal to the desired level and volume for the cup.

Figure 2:
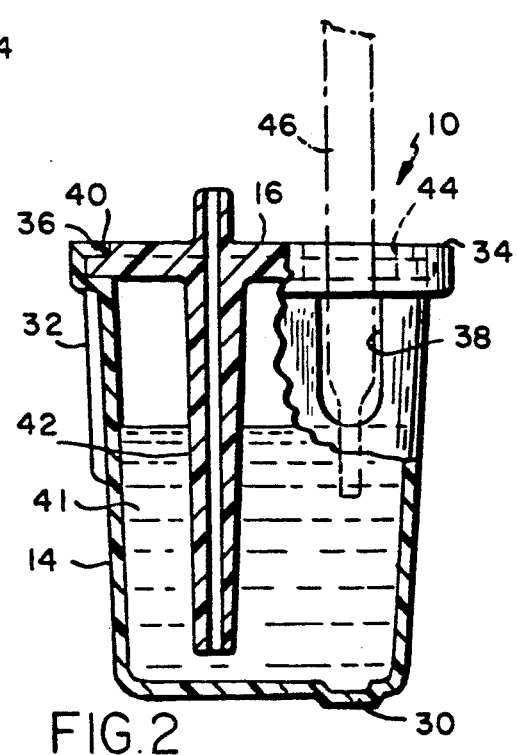
FIG. 2 is a cut-away side view of the diluent cup shown in FIG. 1, with a pipette probe shown in dotted lins.

Cap 16 is, as can be best seen in FIG. 2, sized to snap fit into lip 34. An orientation notch 40 in cap 16 coacts with projection 36 of the lip to assure that cap 16 is attached in the proper orientation. Cap 16 is formed with a hollow straw 42 forming a part thereof. Straw 42 extends substantially perpendicular to cap 16 and has an upper portion which extends slightly above cap 16 and a lower portion which, as can be best seen in FIG. 2, extends into cup portion 14 when cap 16 is mounted therein to a depth near the bottom of the cup portion. The portion of straw 42 extending above the cap may be attached through tubing or other suitable means to a source of diluent fluid or other fluid which is to be contained by the cup. For example, straw 42 could be connected to a source of saline water. Cap 16 also has a generally circular opening 44 formed therein through which a probe 46 may pass to enter the cup portion and access the fluid contained therein. As may be best seen in FIG. 2, when probe 46 is in opening 44, the probe is adjacent notch 38. Lower cup portion 14 and cap 16 may be formed of a plastic such as polypropylene.

While not shown in FIG. 1, support 12 may also include an additional recess containing a wash cup in which probe 46 may be immersed to clean the probe, removing most of the blood or other bodily fluids on the inside and outside thereof before insertion into cup portion 14. Suitable electronic means, known in the art, may also be provided to detect the fluid level in cup portion 14 and thereby control the depth to which probe 46 is inserted therein.

In operation, cap 16 is snap fitted to cup portion 14 with projection 36 in notch 40 assuring proper orientation between the cap and cup portion. A tube attached to a source of fluid to be used in the cup, such as, for example, a saline water solution, may be attached to straw 42 either before or after the cap is attached to the cup portion. The cup portion is then inserted in recess 18 in support 12 with projection 32 and notch 20 assuring that the cup is inserted with notch 38 adjacent channel 22 leading to drain chamber 24. A suitable drain tube would be connected to drain pipe 26.

When all elements are in place, fluid may be applied from a suitable source through straw 42 to the bottom of cup portion 14. Fluid may be applied continuously at a slow rate, with excess fluid overflowing through notch 38 so that there is always a known volume and therefore level of fluid 41 in cup portion 14. Alternatively, between pipetting operations by probe 46, a sufficient quantity of fluid can be applied through straw 42 to cup portion 14 so that the cup is filled to overflowing through notch 38.

When a pipetting operation is to be performed, probe 46 is inserted into cup portion 14 through opening 44 in cap 16. The probe may be inserted until it almost bottoms in well 30 assuring that all of the fluid in cup portion 14, except for a small known dead volume in well 30, may be removed from the cup. However, as shown in FIG. 2, the probe would generally only be inserted to a depth sufficient to extract a desired quantity of the fluid.

As previously indicated, one problem with apparatus 10 is that bodily fluids taken into probe 46 may adhere to the inside or outside of the probe and may not be completely removed by a preliminary wash operation. Therefore, some body fluid from a sample may remain in cup 14 after a pipetting operation, particularly if all of the fluid in cup portion 14 is not removed during the operation. This residual body fluid could contaminate a future sample which is, for example, diluted from the same cup. It is, therefore, important that this contaminating body fluid be removed from cup 14 before a subsequent sample is taken.

Figure 3:
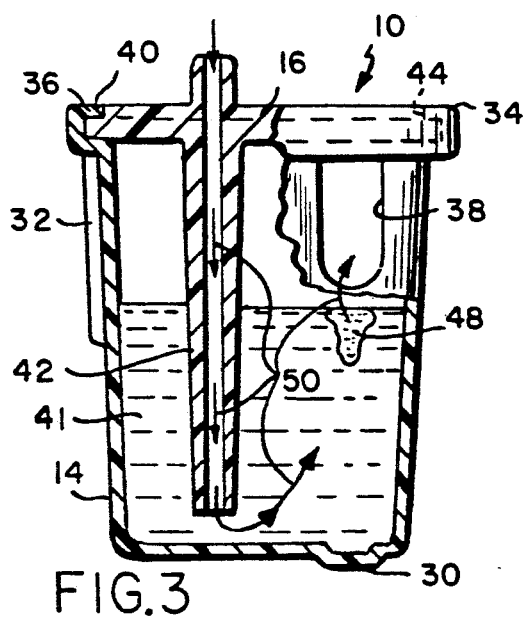
FIG. 3 is a cut away side view of the diluent cup shown in FIG. 1 after the probe has been removed.

Fortunately, experimental evidence shows that such residue from the probe remains in the area of probe penetration, which is generally near the top of the cup, for some period of time, generally several seconds, before diffusing into the dilutant solution. An exemplary residue 48 is shown in FIG. 3. By introducing the desired fluid to the bottom of cup portion 14 just after the probe is removed, a flow is created, as illustrated by arrows 50, which causes the contaminated dilutant to be flushed out through notch 38. The overflow through notch 38 is drained through channel 22, chamber 24 and pipe 26. This contaminant removal effect is optimized by notch 38 being located adjacent to the probe penetration area which is generally approximately ¼ inch below the liquid surface of cup portion 14. Thus, the possibility of contaminants from a prior sample remaining in cup 14 and being taken in by probe 46 for mixing with a later sample is substantially eliminated. Further, since overflow notch 38 is adjacent the contaminant 48 when flow 50 begins, the contaminating residue may be quickly flushed through notch 38 without wasting large quantities of fluid 41 to effect the flush.

An improved cup for use with pipetting or similar systems is thus provided which assures that contaminants are not passed with diluent from one sample to another. While for the preferred embodiment a single notch 38 has been shown in one side of cup portion 14 for overflow purposes, it is apparent that, with a suitable channeling in receptacle slot 12, notches 38 could be provided on both sides of cup portion 14 or any other location or locations in the upper part of cut portion 14. Further, the exact shape of the notches 38 could also vary and holes, slots, or other openings could, in some circumstances, be substituted for the notches 38. The exact manner in which proper orientation is assured for cup portion 14 in recess 18 and for cap 16 on cup portion 14 are, again, matters of design choice and other suitable means for performing these functions could be utilized. Similarly, other suitable means could be provided in place of straw 42 for directing fluid to the bottom of cup portion 14 to establish flow pattern 50. Thus, while the invention has been particularly shown and described above with reference to a preferred embodiment, the foregoing and other changes in form and detail may be made therein by one skilled in the art without departing from the spirit and scope of the invention.

What is claimed is:

1. A cup for holding up to a selected volume of a fluid to be successively aspirated and adapted for use with a support having a fluid drain means and a cup-receiving recess adjacent the drain means, the cup comprising:

a lower cup portion sized to fit in the recess, said cup portion having a bottom and side walls extending upward from said bottom, said side walls terminating in a top lip;

a cap mounted to said lip;

a straw passing through said cap, an opening in said cap for providing access by an aspirating probe to fluid in said cup, contaminants being potentially introduced into the fluid by the probe, said opening being spaced from the straw; and means for flushing the contaminants from said cup, said means including an overflow notch formed in an upper part of one of said side walls, said notch being substantially positioned in the portion of said side wall which is closest to the opening in said cap; said notch having a depth such that the volume capacity of said lower cup portion below said notch is substantially equal to the selected fluid volume, said straw having a lower end extending to a point below said notch and having an upper end extending beyond said cap and said top lip, the fluid being selectively applied to said upper end of said straw, said lower cup portion being sized and shaped to be mountable in the recess with said notch adjacent the drain means, whereby when fluid is introduced to said lower cup portion through said straw at a point below said notch after the probe has been removed, any of the fluid containing contaminants overflows from said cup through said notch.

2. A cup for holding up to a selected volume of a fluid to be successively aspirated and adapted for use with a support having a cup receiving means and drain means, the cup comprising:
   a cap mounted to said lip;
   an opening in said cap for providing access by an aspirating probe to fluid in said cup, contaminants being potentially introduced into the fluid by the probe;
   means for introducing fluid to said bottom of said cup portion; and
   means for flushing the contaminants from the fluid in said cup, said flushing means including means formed in one of said sides of said cup portion adjacent said opening in said cap for permitting fluid in said cup portion in the area passed through by the probe and above a certain depth to overflow to the drain means, the certain depth being the fluid depth in said cup portion required for said cup portion to hold the selected volume of fluid, said fluid being introduced by said introducing means at a depth below said certain depth.

3. A cup as claimed in claim 2 wherein said means for permitting fluid overflow includes a notch extending from said top lip to the certain depth which is formed in one side of said cup portion.

4. A cup as claimed in claim 3 including means for orienting said cup portion in the cup receiving means with said notch adjacent the drain means.

5. A cup as claimed in claim 2 wherein said cap has a straw secured thereto in a position substantially perpendicular to said cap, said straw being spaced from said opening in said cap; and
   wherein said means for introducing fluid includes said straw, which, when said cap is mounted to said top lip, has a lower end extending below said certain depth and an upper end extending beyond said top lip of said cup portion, fluid being applied to said upper end of said straw.

* * * * *

UNITED STATES PATENT AND TRADEMARK OFFICE
CERTIFICATE OF CORRECTION

PATENT NO. : 5,156,813
DATED : October 20, 1992
INVENTOR(S) : Jeffrey Calhoun

It is certified that error appears in the above-indentified patent and that said Letters Patent is hereby corrected as shown below:

Column 5 & 6, lines 1-22, claim 2, should read

2. A cup for holding up to a selected volume of a fluid to be successively aspirated and adapted for use with a support having a cup receiving means and drain means, the cup comprising:
    a lower cup portion sized to fit in the cup-receiving means, said cup portion having sides, a top lip and a bottom;
    a cap mounted to said lip;
    an opening in said cap for providing access by an aspirating probe to fluid in said cup, contaminants being potentially introduced into the fluid by the probe;
    means for introducing fluid to said bottom of said cup portion; and

UNITED STATES PATENT AND TRADEMARK OFFICE
CERTIFICATE OF CORRECTION

PATENT NO.   : 5,156,813
DATED        : October 20, 1992
INVENTOR(S)  : Jeffrey Calhoun It is certified that error appears in the above-indentified patent and that said Letters Patent is hereby corrected as shown below:

means for flushing the contaminants from the fluid in said cup, said flushing means including means formed in one of said sides of said cup portion adjacent said opening in said cap for permitting fluid in said cup portion in the area passed through by the probe and above a certain depth to overflow to the drain means, the certain depth being the fluid depth in said cup portion required for said cup portion to hold the selected volume of fluid, said fluid being introduced by said introducing means at a depth below said certain depth.

Signed and Sealed this

Twenty-first Day of November, 1995

Attest:

BRUCE LEHMAN

*Attesting Officer*   *Commissioner of Patents and Trademarks*